United States Patent [19]
Cepuritis et al.

[11] 3,989,047
[45] Nov. 2, 1976

[54] DIAPER WITH LOOP-TYPE ADHESIVE FASTENER

[75] Inventors: Talivaldis Cepuritis, Kenilworth; Ludwig Tritsch, Wilmette, both of Ill.

[73] Assignee: Johnson & Johnson, New Brunswick, N.J.

[22] Filed: Sept. 29, 1975

[21] Appl. No.: 617,914

[52] U.S. Cl. .............................. 128/287; 128/284
[51] Int. Cl.² ................... A61F 13/16; A41B 13/02
[58] Field of Search .............. 128/284, 287, 290 R; 24/67, 73 VA, DIG. 11

[56] References Cited
UNITED STATES PATENTS

| | | | |
|---|---|---|---|
| 3,646,937 | 3/1972 | Gellert | 128/287 |
| 3,750,669 | 8/1973 | DeLuca | 128/287 |
| 3,776,234 | 12/1973 | Hoey | 128/287 |
| 3,794,038 | 2/1974 | Buell | 128/287 |
| 3,810,472 | 5/1974 | Aldinger | 128/287 |
| 3,848,594 | 11/1974 | Buell | 128/284 |
| 3,869,761 | 3/1975 | Schaar | 24/73 VA |
| 3,900,031 | 8/1975 | Endres | 128/287 |
| 3,930,503 | 1/1976 | Tritsch | 128/287 |
| 3,931,666 | 1/1976 | Karami | 128/287 X |

Primary Examiner—Aldrich F. Medbery

[57] ABSTRACT

A disposable diaper having a facing sheet defining a diaper inside surface for direction toward an infant and a backing sheet defining a diaper outside surface is provided with adhesive tabs comprising an elongated tape segment folded over to form a loop having an inner face and an outer face, the tabs including first and second terminal portions and a central portion integral with the terminal portions. The tape segment receives a marginal portion of the diaper between the terminal portions and is permanently attached to the facing and backing sheets by means of adhesive coatings on opposing inner faces of the terminal portions. An adhesive coating is provided on the outer face of the central portion of the tape segment, is releasably attached to a release region provided on the diaper inside surface, and the central portion of the tab is movable from a folded-over storage position wherein the adhesive-coated central portion is releasably adhered to the release region to a working position wherein the adhesive-coated central portion is available for use in securing the diaper about an infant. Secondary fastening means may be provided for refastening the diaper about the infant by positioning a second adhesive coating and second release means on the inside surface of the central portion. Lines of weakening may be provided in a tab having secondary fastening means to facilitate repositioning of the diaper about the infant.

17 Claims, 6 Drawing Figures

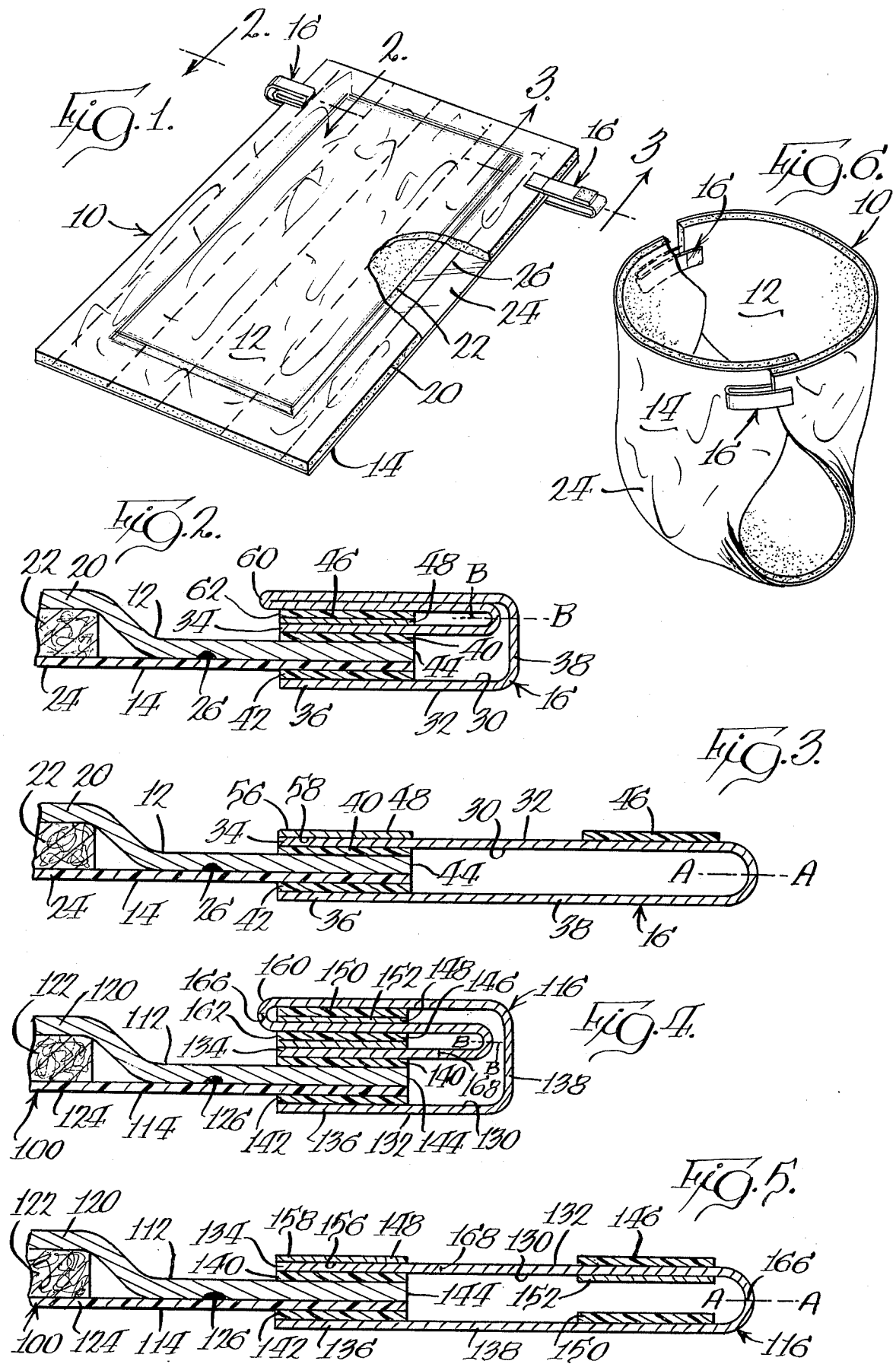

DIAPER WITH LOOP-TYPE ADHESIVE FASTENER

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefore, generally made of a plastic film such as polyethylene film or the like. Typical disposable diaper structures are shown in U.S. Pat. No. 3,612,055 to Mesek et al. and in U.S. Pat. No. Re.26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fasetning tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two coextensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

SUMMARY OF THE INVENTION

According to the present invention, a single tape tab segment is used on each side of a diaper to secure the diaper about an infant. The tab is folded-over to form a loop having an inner face and an outer face, and includes first and second terminal portions and a central portion integral with the terminal portions. The tab receives a marginal portion of the diaper between the terminal portions and is permanently attached to the facing and backing sheets by means of adhesive coatings on opposing inner faces of the terminal portions. A first pressure-sensitive adhesive coating is provided on the outer face of the central portion of the tab. A release means which provides a release region is positioned at a marginal location on the diaper inside surface, and may be on the first terminal portion. The central portion of the tab is movable from a folded-over storage position, wherein the first adhesive is releasably adhered to the release region, to a working position wherein the adhesive-coated central portion of the tab is available for use in securing the diaper about an infant.

The tab may also be provided with secondary fastening means for refastening the diaper about the infant. The secondary fastening means comprises a second pressure-sensitive adhesive coating and a second release means, both of which are provided in substantially juxtaposed relation on the inner face of the central portion of the tab. To facilitate repositioning of the diaper about the infant, lines of weakening may be provided in the tab. For example, a line of weakening may be provided between the first and second adhesive coatings. Thus, after securing the diaper about an infant, the tab can be severed, and the diaper can thereafter be repositioned on the infant by employing the second adhesive coating.

The release means may comprise a release coating printed or otherwise deposited on a portion of the diaper inside surface, a release strip having a release coating on one face thereof and an adhesive coating on the opposite face by means of which the release strip is adhered to the diaper. Other suitable means for releasably adhering the central portion of the tab to the diaper can also be employed. Gripping means may also be provided on the tab to facilitate separation of the central portion of the tab from the release means preparatory to fastening the diaper about an infant.

The tape tab fasteners of the present invention remain flat against the diaper when in the folded configuration and will not interfere with the diaper manufacturing machinery and the subsequent folding and packaging operations. Additional features of this invention include the utilization of an integral tape tab which is relatively easy to affix to the diaper and provides good bond strength, and permanent attachment of the tab to both the diaper facing sheet and backing sheet so that when stress is imposed on the tab free end which fastens the diaper, the stress is distributed between the facing sheet and the backing sheet, thereby reducing the possibility of undesirable rupture of the backing sheet.

BRIEF DESCRIPTION OF THE DRAWINGS

FIG. 1 is a perspective view, partially broken away to show interior detail, of an open unfolded diaper in accordance with one of the embodiments of the invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3;

FIG. 4 is a fragmentary cross-sectional view, similar to FIG. 2, and illustrating an alternate embodiment of the invention in the folded-over storage position;

FIG. 5 is a fragmentary cross-sectional view, similar to FIG. 3, and illustrating the embodiment of FIG. 4 in the working position; and FIG. 6 is a perspective view of the diaper of FIG. 1 in a configuration assumed by the diaper when placed about an infant.

DESCRIPTION OF THE PREFERRED EMBODIMENTS

In the following description, two digit numerals are used to refer to the embodiment illustrated in FIGS. 1–3 and 6, and three digit numerals in the one hundred series are used to refer to the embodiment illustrated in FIGS. 4 and 5, the same last two digits in each numeral designating similar elements in the various embodiments.

Disposable diaper 10, illustrated in FIGS. 1 and 6, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to a working position which is illustrated in FIG. 3.

Referring to FIGS. 1–3, diaper 10 comprises moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made coextensive with backing sheet 24, if desired. Facing sheet 20 is substantially co-extensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 comprises an elongated tape segment which is folded over about a first fold line A—A so as to form a loop having an inner face 30 and an outer face 32. Tab 16 has first and second terminal portions 34, 36 and a flexible central portion 38 which is integral with the terminal portions. Terminal portions 34, 36 preferably are about equal in width and length and are in a substantially juxtaposed relationship to one another. The inner faces of the first and second terminal portions 34, 36 both are part of inner face 30, face each other and are provided with an adhesive coating 40, 42 by means of which tab 16 is attached to diaper 10. Tab 16 receives a marginal portion of diaper 10 between terminal portions 34, 36, the first terminal portion 34 being permanently attached to facing sheet 20 by means of adhesive coating 40, and second terminal portion 36 being permanently attached to backing sheet 24 by means of adhesive coating 42, so that stresses exerted on tab 16 are distributed to both surfaces of the diaper. Adhesive coatings 40, 42 can be made of a pressure-sensitive adhesive composition, a heat-activated or solvent-activated adhesive composition, or the like.

Tab 16 is folded about longitudinal edge 44 of diaper 10 by folding the loop over about a second fold line B—B to the storage position illustrated in FIG. 2 and is adapted for movement from the storage position to a working position illustrated in FIG. 3. First pressure-sensitive adhesive coating 46 is provided on outer face 32 of central portion 38 between first fold line A—A and first terminal portion 34, faces in the same direction as the diaper inside surface 12 when tab 16 is in the working position, and provides a securement means which can be moved from the closed, storage position of FIG. 2 to the open working position of FIG. 3 for fastening the diaper about an infant.

A first release means 48 is provided and is adapted to be releasably attached to adhesive coating 46. The release means may be carried by diaper 10 at a marginal location thereon to provide a release region on diaper inside surface 12. When tab 16 is in the storage position of FIG. 2, adhesive coating 46 on central portion 38 is releasably adhered to first release means 48.

In the embodiment illustrated in FIGS. 4 and 5, second pressure-sensitive adhesive coating 150 and second release means 152 are provided on portions of inner face 130 of central portion 138 to provide means for refastening diaper 100 about an infant after the diaper has been placed on the infant. A first line of weakening 166 is provided in central portion 138 between first adhesive coating 146 and second adhesive coating 150 and may be substantially along first fold line A—A which divides the central portion into two substantially co-extensive half-portions. The second pressure-sensitive adhesive coating 150 is positioned on the half-portion situated between first line of weakening 166 and second terminal portion 136, and the second release means 152 is positioned on the half-portion situated between first line of weakening 166 and first terminal portion 134, the second pressure-sensitive adhesive coating 150 being in substantially juxtaposed relation to and releasably adhered to second release means 152. After securing diaper 100 about an infant, tab 116 can be severed along first line of weakening 166, and diaper 100 can thereafter be refastened about the infant by employing second adhesive coating 150.

The embodiment illustrated in FIGS. 4 and 5 preferably includes a second line of weakening 168 which is provided transversely across central portion 138 of tab 116 between first terminal portion 134 and first pressure-sensitive adhesive coating 146 and may be substantially along second fold line B—B.

Both first and second lines of weakening 166, 168 facilitate in removal of diaper 100 from an infant. By severing tab 116 along both the first and second lines of weakening, the diaper can be completely removed from an infant and thereafter refastened on the infant by utilizing the second adhesive coating 150.

Release means, such as first release means 48, may comprise a ribbon segment or release strip carried by first terminal portion 34 and provided with a release coated face 56 which provides the release region, and an adhesive coating on opposite face 58 by means of which the release strip is anchored to first terminal portion 34 on diaper inside surface 12. Release coated face 56 faces in the same direction as diaper inside surface 12 and is substantially co-extensive with adhesive coating 46 on central portion 38 when tab 16 is folded to the storage position. Alternatively, release means 48 may comprise a release coating, such as a silicone release compound, or the like, on outer face 32 of first terminal portion 34 and which is substantially co-extensive with adhesive coating 46 on central portion 38 when tab 16 is folded to the storage position. Similarly, second release means 152 may comprise a ribbon segment or a release coating, the second adhesive coating 150 being juxtaposed to second release means 152 when tab 116 is in the working position.

It is desirable to provide a gripping means to facilitate grasping tab 16 to separate the portion of tab 16 having adhesive coating 46 from first release means 48 preparatory to fastening the diaper about an infant. As shown in FIG. 2, central portion 38 includes a projecting portion 60 which extends inwardly on diaper 10 beyond outermost margin or end 62 of adhesive coating 46 when tab 16 is in the storage position. The outwardly extending segment 60 provides a gripping means for separating first adhesive coating 46 on central portion 38 from first release means 48 when fastening diaper 10 about an infant.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 46 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dipersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75 to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially co-extensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re.26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling central portion 38 away from its temporary engagement with release means 48, exposing adhesive coating 46 which was releasably adhered to release means 48 and separable therefrom. The tabs are then used to secure the diaper in the desired position by simply urging the pressure-sensitive adhesive surfaces in contact with the adjacent outer surface of the diaper. The applied diaper assumes the configuration illustrated in FIG. 6.

The foregoing description and the drawing are illustrative but are not to be taken as limiting. Still other variations and modifications are possible without departing from the spirit and scope of the present invention.

We claim:

1. A disposable diaper having a facing sheet defining a diaper inside surface for direction toward an infant, a moisture-impervious backing sheet substantially co-extensive with said facing sheet and defining a diaper outside surface, an absorbent panel positioned between said facing sheet and said backing sheet, and an adhesive tab fastener means which comprises:
   an elongated tape segment folded over about a first fold line so as to form a loop substantially open when extended and having an inner face and an outer face, having first and second terminal portions and a flexible central portion integral with said terminal portions, and attached to said diaper at a marginal location adjacent to one end of the diaper;
   an adhesive coating on the surfaces of said terminal portions which face each other; and
   a first pressure-sensitive adhesive coating on the outer face of said central portion;
   first release means on said inside surface for releasable attachment to said first adhesive coating on said central portion;
   said tape segment receiving a marginal portion of said diaper between said terminal portions, said first terminal portion being permanently attached to said facing sheet, and said second terminal portion being permanently attached to said backing sheet by means of said adhesive coatings;
   said central portion being separable from said release means to make said adhesive coating on said central portion available for use in securing said diaper about an infant.

2. The disposable diaper as defined in claim 1 wherein said first and second terminal portions are about equal in width and length and are in a substantially juxtaposed relationship to one another.

3. The disposable diaper as defined in claim 1 wherein said first fold line divides said central portion into two substantially co-extensive half-portions, wherein a first line of weakening is provided substantially transversely across said central portion, and wherein the half-portion situated between said line of weakening and said second terminal portion is provided on the inner face thereof with a second pressure-sensitive adhesive coating.

4. The disposable diaper as defined in claim 3 wherein a second line of weakening is provided substantially transversely across said tape segment between said first terminal portion and said first pressure-sensitive adhesive coating on said central portion.

5. The disposable diaper as defined in claim 3 wherein a second release region is provided on the inner face of the half-portion situated between said first line of weakening and said first terminal portion, and wherein said second pressure-sensitive adhesive coating is releasably adhered to said second release region.

6. The disposable diaper as defined in claim 1 wherein said first release means is carried by said diaper at a marginal location thereon and provides a release region facing in the same direction as said diaper inside surface,
   said loop being adapted for folding over about a second fold line from a storage position wherein said central portion is releasable adhered to said first release means to a working position wherein said first adhesive coating on said central portion is available for use in securing said diaper about an infant.

7. The disposable diaper as defined in claim 6 wherein said first adhesive coating on said central portion faces in the same direction as said diaper inside surface when said tab fastener means is extended to said working position.

8. The disposable diaper as defined in claim 6 wherein said release means is a release coating on the outer face of said first terminal portion and is substantially coextensive with said first adhesive coating on said central portion when said loop is folded to the storage position.

9. The disposable diaper as defined in claim 8 wherein said release coating comprises a silicone release compound.

10. The disposable diaper as defined in claim 6 wherein said release means comprises a ribbon segment carried by said first terminal portion and provided with a release coating facing in the same direction as said diaper inside surface and substantially coextensive with said adhesive coating on said central portion when said loop is folded to the storage position.

11. The disposable diaper as defined in claim 6 wherein said central portion includes a segment on opposite sides of said first fold line which segment projects inwardly beyond said adhesive coating on said central portion when said central portion is in said storage position, whereby said projecting segment provides a gripping means for separating said first adhesive coating on said central portion from said first release means when fastening said diaper about said infant.

12. The disposable diaper as defined in claim 1 wherein said first fold line in said tape segment divides said central section into two substantially coextensive half-portions, said first pressure-sensitive adhesive coating being disposed on the half-portion between the first fold line and the first terminal portion;
wherein the half-portion between the first fold line and the second terminal portion is provided with a second pressure-sensitive adhesive coating on at least a portion of the inner face thereof;
wherein the half-portion between the first fold line and the first terminal portion is provided with a second release means on said inner surface thereof; and
wherein a line of weakening is provided in said tape segment between said first and second pressure-sensitive adhesive coatings and between said first pressure-sensitive adhesive coating and said first terminal portion;
said second pressure-sensitive adhesive coating and said second release means being in substantially juxtaposed relation when said diaper is in said folded-over storage position;
whereby said diaper can be repositioned about an infant by severing said tape segment along said lines of weakening, and thereafter refastening the diaper about said infant by utilizing said second adhesive coating.

13. The disposable diaper as defined in claim 12 wherein said central portion of said tape segment is provided with a first line of weakening substantially along said first fold line.

14. The disposable diaper as defined in claim 13 wherein said central portion of said tape segment is provided with a second line of weakening substantially along a second fold line about which said loop is adapted for folding to a storage position.

15. The disposable diaper as defined in claim 12 wherein said second release means is a release coating.

16. The disposable diaper as defined in claim 15 wherein said release coating comprises a silicone release compound.

17. The disposable diaper as defined in claim 12 wherein said second release means comprises a ribbon segment carried by said half-portion between the first fold line and the first terminal portion.

* * * * *